United States Patent [19]

Walter et al.

[11] 4,147,921
[45] Apr. 3, 1979

[54] HEAT TREATING ARTICLES

[75] Inventors: Henry J. Walter, Wilton; Raymond W. Kunz, Monroe, both of Conn.

[73] Assignee: Clairol Inc., New York, N.Y.

[21] Appl. No.: 831,839

[22] Filed: Sep. 9, 1977

[51] Int. Cl.$^2$ .............................................. H05B 1/00
[52] U.S. Cl. ................................... 219/211; 128/380; 219/527; 219/535; 219/540
[58] Field of Search ............... 219/211, 222, 530, 535, 219/540, 527, 528, 529; 126/204, 400; 128/379, 380, 410; 34/95.1, 96; 2/174, 198; 132/7, 9

[56] References Cited

U.S. PATENT DOCUMENTS

| | | | |
|---|---|---|---|
| 2,470,833 | 5/1949 | Moore | 34/95.1 |
| 2,493,363 | 1/1950 | Sapp | 34/95.1 |
| 2,584,302 | 2/1952 | Stein | 219/535 X |
| 3,347,248 | 10/1967 | Weitzner | 219/222 X |
| 3,548,930 | 12/1970 | Byrd | 219/530 X |
| 3,559,658 | 2/1971 | Genest et al. | 219/222 X |
| 3,764,780 | 10/1973 | Ellis | 219/530 X |
| 3,988,568 | 10/1976 | Mantell | 219/527 X |
| 4,061,898 | 12/1977 | Murray et al. | 219/527 X |

*Primary Examiner*—C. L. Albritton
*Attorney, Agent, or Firm*—John A. Caruso; George A. Mentis; David J. Mugford

[57] ABSTRACT

An electrically heatable article containing a layer of wax and adapted to conform to the shape of a body surface, when the wax is melted, for thereafter treating the body surface with the heat of fusion of the wax. In an article, such as a head treatment cap, the wax is contained in a layer of modules arranged near the scalp side of the cap, a resistance heating element is provided for initially heating the wax to its melting point, and insulation is provided for preventing heat loss through the outside of the cap.

15 Claims, 12 Drawing Figures

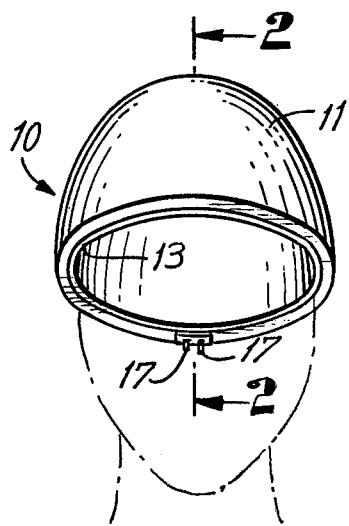
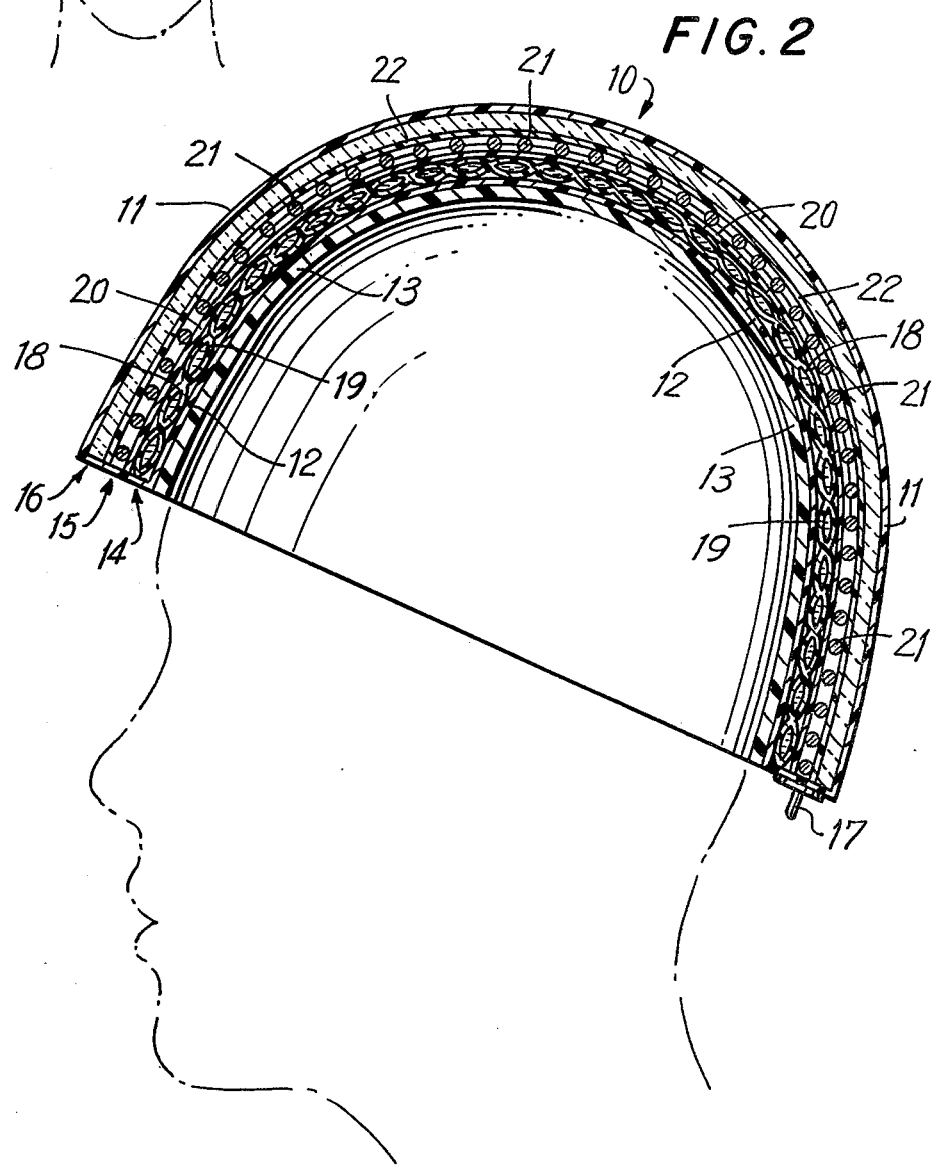

HEAT TREATING ARTICLES

BACKGROUND OF THE INVENTION

This invention relates to heat treating articles. More particularly, it relates to an article which can initially be heated, by one of several conventional electrical resistance heating means, to melt a layer of wax therein and then be aplied to a particular area of the body to treat that area with the heat of fusion of the wax as it resolidifies.

One type of heating pad, cap, blanket, or similar article for body treatment is well known. Generally, such an article is heated by a resistance heating means activated by an electrical cord delivering electrical current from a power source into the article. In using such an article, it is heated to a particular temperature and applied to the body area to be treated, during which time the heating means maintain the desired treatment temperature. The disadvantage of this type of heat treating article is that the electrical heating means must be maintained in operation during the treatment, which may restrict movement of the article or person being treated.

Another type of heat treating article is known which may initially be heated to a desired temperature, then disconnected from the heating means, and thereafter applied to the person's body to provide heat treatment by means of heat retained in the article. U.S. Pat. No. 3,463,161 discloses temperature maintaining devices which employ as a heat retaining material an aqueous composition of a soap, an emulsifying agent, and parrafin. U.S. Pat. Nos. 3,437,095 and 3,594,915 disclose head treatment caps utilizing a layer of, generally, a fibrous material for heat retention. U.S. Pat. Nos. 2,420,358; 2,453,179; 2,470,833; 2,493,363; 2,919,494; and 3,902,508 disclose head treatment caps utilizing, generally, a silica gel as a heat retaining material. U.S. Pat. Nos. 3,257,541; 3,410,985; and 3,485,248 disclose rigid, hair rollers utilizing, generally, wax as a heat retaining material. Other known U.S. state of the art patents are U.S. Pat. Nos. 1,710,882; 2,173,683; 2,178,397; 2,488,793; 2,460,433; 2,783,806; 3,839,621; and 3,869,594.

The heat treating articles of this invention utilize essentially wax as a heat retaining material and utilize conventional electrical heating means for only initially melting the wax, after which the heating means may be removed so that the article and person being treated can move and be moved about freely while the heat of fusion of the wax provides heat treatment.

SUMMARY OF THE INVENTION

A heat treating article adapted to conform to the body surface to be treated is provided. The article includes flexible inner and outer covers, a layer of wax, preferably enclosed in modules, arranged near the inner cover of the cap, heating elements disposed around, within, or in close contact with the wax layer and at least one layer of insulation for preventing heat loss through the outer cover of the article. The heating elements of the article are electrically activated by means, such as an electrical cord connected to a power source, for initially melting the wax, after which the cord may be disconnected from the article. Upon being applied to the body surface, the heat of fusion of the melted wax treats the body surface at a desired treatment temperature.

BRIEF DESCRIPTION OF THE DRAWINGS

Heat treating articles of this invention are described in detail below and reference should be made to the drawings thereof herein which are as follows:

FIG. 1 is a perspective view of a heat treatment cap of the present invention as it would be applied to a person's head.

FIG. 2 is a cross sectional view along lines 2—2 of the cap of FIG. 1.

DETAILED DESCRIPTION OF THE PREFERRED EMBODIMENTS

Figure 3:
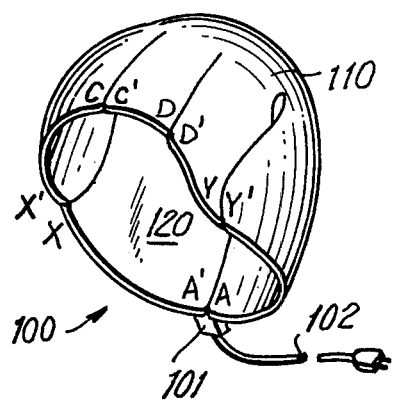
FIG. 3 is a perspective view of another heat treatment cap of the present invention.

A heat treating article of this invention, namely a hair treatment cap 10, is shown in FIG. 1. The cap has an outer cover 11 and an inner cover 12, which is shown best in and described below with regard to FIG. 2. Covers 11 and 12 are preferably made from vinyl, plastic, or another polymeric material essentially impermeable to moisture.

As shown in FIG. 1, a sanitary cap 13, which is preferably separate from cap 10, may be placed on the user's head prior to the placement thereon of cap 10 to eliminate the need for cleaning cap 10 itself of any hair treatment products which may have been used. Separate cap 13 could be made of an easily washable material to facilitate removal of such products from it. Preferably, cap 13 is made of a single layer of plastic or of a tightly knit material.

Referring particularly to FIG. 2, inner and outer covers 11 and 12 are joined and enclose therebetween the heat treating components of cap 10. Proceeding from the scalp or inner side of the cap to the outside of cap 10, there is provided a wax layer, a heating element layer, and an insulation layer, generally indicated at 14, 15 and 16, respectively. Additionally, an electrical connector having terminals 17, which are in electrical contact with the heating elements of layer 15, is provided for receiving an electrical cord by which the heating elements may be activated for initially heating the cap, as described below.

Turning now to wax layer 14, a wax having a predetermined melting point is confined between sheets 18 and 19. As shown in FIG. 2, the sheets are sealed to provide a modular effect, which gives the wax layer enhanced flexibility. The sheets are preferably made of a flexible material, such as vinyl, felt, or vinyl and felt.

Outward of wax layer 14 is a barrier 20 separating the wax layer from heating element layer 15. Barrier 20 is preferably made of vinyl, felt, or vinyl and felt. Heating element layer 15 contains a rope heater 21, one end of which, at the rear portion of cap 10 preferably, is in electrical contact with terminals 17. Although, as shown in FIG. 2, heater 21 is confined between barrier 20 and another similar barrier 22, which is disposed between layers 15 and 16, a heater can be sewn or printed onto one of the barriers so that the other barrier can be eliminated.

Insulation layer 16 is composed of substantially one or more materials which will prevent movement towards or loss of heat generated by heating elements 21 through the outside of the cap. Preferably, air trapping fibers, a heat reflective film, or similar non-heat absorbing material that helps prevent cooling of the wax once it is melted is used.

Another heat treating cap of this invention, generally indicated at 100, is shown in FIG. 3. This cap utilizes essentially the same components as does the cap of FIG. 1; namely a wax layer, heating elements, and an insulation layer, all enclosed within inner and outer covers.

At the rear portion of cap 100, electrical terminals (not shown) extend outwardly and are received by an electrical connector 101 having a conventional electrical cord 102 attached thereto. The cap has an outer cover 110 and an inner cover 120. Rather than the covers being continuous, as was the case with the covers of the cap of FIG. 1, covers 110 and 120 are discontinuous, as shown in FIG. 4.

Figure 4:
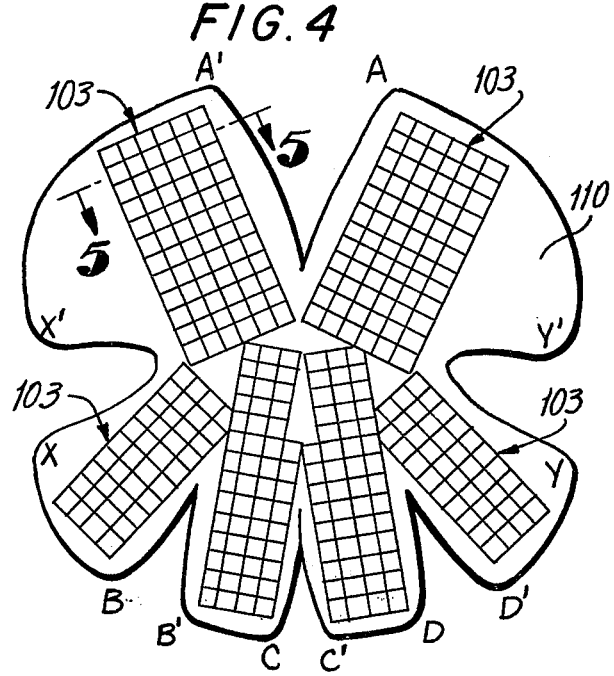
FIG. 4 is a view of the cap of FIG. 3 in its unassembled condition.

Essentially, the periphery of each of the covers is discontinuous because the components of this cap do not extend throughout the cap, as in the cap of FIG. 1, but rather are arranged in numerous grids, each indicated at 103 in FIG. 4. Although the grids are somewhat spaced apart and do not completely cover the cap in its unassembled condition, when the cap is assembled, as shown in FIG. 3, grids 103 become more closely arranged to contact essentially the entire area of the user's head, similar to the cap of FIG. 1.

Figure 6:
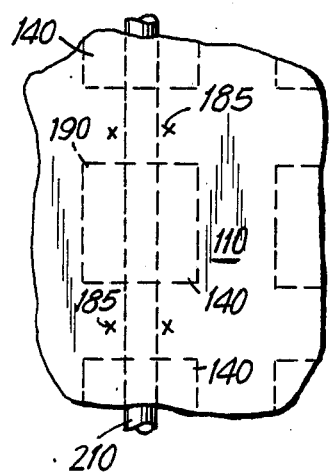
FIG. 6 is an enlarged, top plan view of predominently the wax modules, heater elements, and insulation of the cap, which is shown in FIG. 5.
Figure 5:
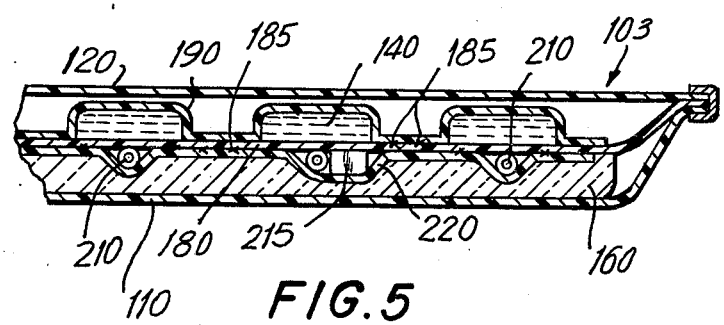
FIG. 5 is a cross sectional view along lines 5—5 of the cap of FIG. 4.

Referring to FIG. 5, a portion of one grid 103 is shown. Closest to the scalp side of the cap or inner cover 120 is a layer of individual wax modules, each indicated at 140. The modules are formed by barriers 180 and 190, which are sealed at various points 185 (best shown in FIG. 6). A heater element 210 and, preferably, a thermostat 215 are supported outwardly of wax modules 140 on a heater support 220, which is sealed to barrier 180. Thus, the heater elements are maintained adjacent to the wax modules because of this confinement between support 220 and barrier 180 to insure sufficient heating of the wax modules. Outwardly of the heating elements is an insulation layer 160 adjacent to outer cover 110.

To use the heat treatment caps of FIGS. 1 and 3, the electrical terminals thereof are connected to a power source by the electrical connector and cord, causing the heater elements to be activated. Preferably after the heater elements have melted the wax, the cap is snugly fit around the user's hair. Once the wax is melted, the electrical connector and cord may be removed. The heat now stored by the wax treats the user's hair as it resolidifies. It has been found that although the inside temperature of the cap may be about 150° to 190° F. while the user's hair is being treated, the outside temperature of the cap is generally below 120° F., so that the cap can be easily handled during the treatment. It has also been found that after the termination of power input into the heater elements, the cap is capable of maintaining dry hair at about 130° F. for about 45 minutes and moist hair at about 120° F. for about 35 minutes. The major reason for these results is the capability of conforming the cap snugly to the particular shape of the user's head to promote most efficient heat transfer thereto from the cap.

It is contemplated that more than one layer of wax modules could be utilized in the caps of this invention and that within a layer or layers of wax modules, waxes having different melting points could be used in different modules to provide for a particular desired multiple temperature operation. Preferably the wax modules are separated by a distance of about twice their thickness to provide maximum flexibility of the cap. Also, a layer of aluminum as a film or foil could be utilized to enhance heat distribution over the modules from the heater elements.

In addition to the arrangements of the wax and heater element layers described above, other arrangements of these layers are contemplated for the caps of this invention, which are illustrated in FIGS. 7-12 similar to FIG. 5.

Figure 7:
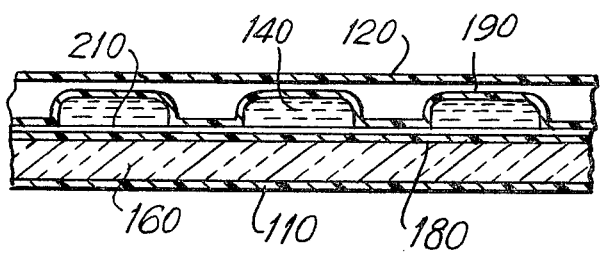
FIG. 7 is a view similar to FIG. 5 of another embodiment of a heat treatment cap of this invention.

Utilizing the same numbers to represent the same structures as employed in FIG. 5, FIG. 7 discloses one alternative arrangement. In this arrangement, heater 210, which is preferably a ribbon heater, not only provides a heating function, but could also function as a wax barrier, if barrier 180 were eliminated. Additionally, a second layer of modules could be used in the arrangement of FIG. 7, similar to that of FIG. 8.

Figure 8:
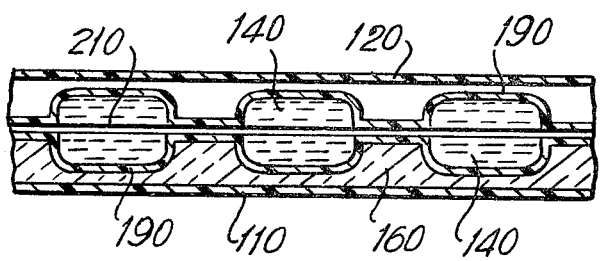
FIG. 8 is a view similar to FIG. 5 of another embodiment of a heat treatment cap of this invention.
Figure 9:
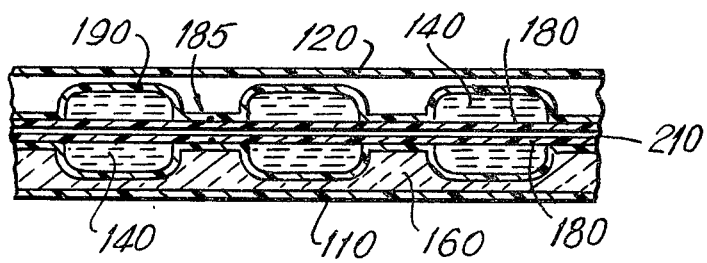
FIG. 9 is a view similar to FIG. 5 of another embodiment of a heat treatment cap of this invention.

In the arrangement of FIG. 8, heater 210 serves both the latter functions and it has been found that with this arrangement, heating is improved while the flex area between the modules is halved relative to the total wax thickness. In the arrangement of FIG. 9, two barriers 180 are employed around heater 210.

Figure 10:
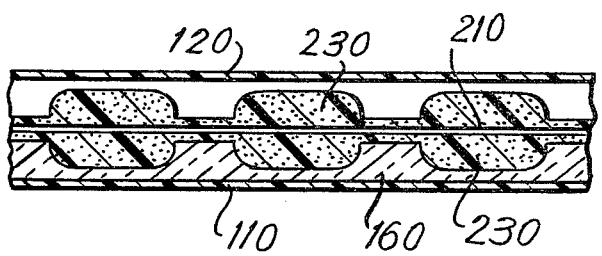
FIG. 10 is a view similar to FIG. 5 of another embodiment of a heat treatment cap of this invention.

In the arrangement of FIG. 10, a ribbon heater 210 is encased within modules formed by an open cell foam or non-woven fabric material indicated at 230, which is preferably a thermoplastic or thermoset coated material. Similarly in FIG. 11 the heater is affixed to a heater support 220 and in FIG. 12, barriers 180 surround heater 210, which in this case is a rope heater.

Figure 11:
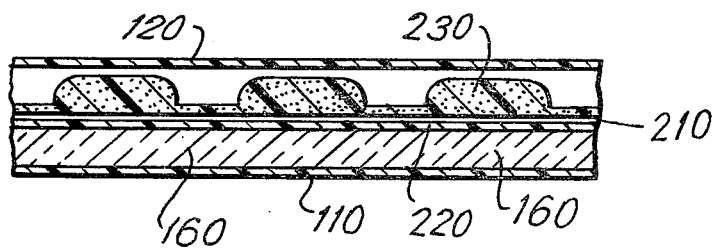
FIG. 11 is a view similar to FIG. 5 of another embodiment of a heat treatment cap of this invention.
Figure 12:
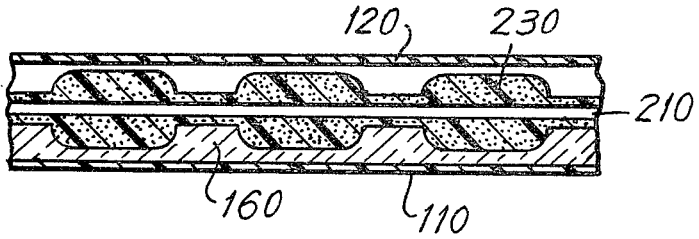
FIG. 12 is a view similar to FIG. 5 of another embodiment of a heat treatment cap of this invention.

Generally, in connection with the above described arrangements, positive sealing of the wax, especially that filled into the modules of FIGS. 10-12, can be enhanced by the provision therearound of barriers of non-permeable plastic or other materials mentioned above. Also, agents, such as those which increase the consistency of the wax in its molten state without substantially changing its thermal characteristics, can be incorporated into the wax layers of these caps to provide the wax therein with particular desired characteristics. Typical agents that can be used are: silicone dioxide, hyproxy propyl cellulose, gum damar, etc.

The heat treating articles of this invention should not be interpreted solely by the preferred embodiments thereof described above, but rather by reference to the claims appended hereto.

What is claimed is:

1. A heat treating article comprising a first flexible cover, a layer of wax, a heating element for melting the wax, a layer of insulation which is substantially nonpermeable to the heat generated by the heating element, and a second flexible cover joined with the first flexible cover to enclose the wax layer, heating element, and insulation layer.

2. The heat treating article of claim 1 wherein the heating element further comprises electrical terminals through which electrical current may be delivered into the article for activating the heating element.

3. The heat treating article of claim 1 wherein the first flexible cover is inside the layer of wax, the heating element is outside the layer of wax, the insulation layer is outside the heating element, and the second flexible cover is outside the insulation layer.

4. The heat treating article of claim 1 further comprising a barrier between the heating element and insulation layer.

5. The heat treating article of claim 4 wherein the heating element is secured to the barrier.

6. The heat treating article of claim 4 further comprising two sheets enclosing the layer of wax.

7. The heat treating article of claim 4 further comprising a barrier between the heating element and the layer of wax.

8. The heat treating article of claim 6 wherein the sheets are sealed to each other at various points to form modules in which the wax is enclosed.

9. The heat treating article of claim 8 wherein one of the sheets and the barrier encloses the heating element and are sealed at the same points as are the two sheets.

10. The heat treating article of claim 8 further comprising a barrier between the modules of wax and the heating element.

11. A heat treating article comprising a first flexible cover, at least one layer of wax, the wax being in modules, a heating element for melting the wax, and a second flexible cover joined with the first flexible cover to enclose the layer of wax and heating element.

12. The heat treating article of claim 11 wherein the first flexible cover is inside the layer of wax, the heating element is outside the layer of wax, and the second flexible cover is outside the heating element.

13. The heat treating article of claim 12 wherein the heating element is within the layer of wax and contacts the wax.

14. The heat treating article of claim 12 wherein the heating element separates the modules of wax.

15. The heat treating article of claim 12 wherein the heating element is sealed within the layer of wax out of contact with the wax.

* * * * *